(12) United States Patent
Proennecke et al.

(10) Patent No.: US 9,967,739 B2
(45) Date of Patent: May 8, 2018

(54) MOBILE VIRTUALIZATION PLATFORM FOR THE REMOTE CONTROL OF A MEDICAL DEVICE

(71) Applicant: DEBIOTECH S.A., Lausanne (CH)

(72) Inventors: Stephan Proennecke, Lausanne (CH); Oscar Francois, Lausanne (CH); Frédéric Neftel, Lausanne (CH)

(73) Assignee: DEBIOTECH S.A., Lausanne (CH)

( * ) Notice: Subject to any disclaimer, the term of this patent is extended or adjusted under 35 U.S.C. 154(b) by 13 days.

(21) Appl. No.: 14/354,697

(22) PCT Filed: Oct. 26, 2012

(86) PCT No.: PCT/IB2012/055917
§ 371 (c)(1),
(2) Date: Apr. 28, 2014

(87) PCT Pub. No.: WO2013/061296
PCT Pub. Date: May 2, 2013

(65) Prior Publication Data
US 2014/0298022 A1    Oct. 2, 2014

(30) Foreign Application Priority Data

Oct. 28, 2011 (EP) .................................... 11187121
Jul. 9, 2012 (EP) .................................... 12175498

(51) Int. Cl.
*H04L 9/32*    (2006.01)
*H04W 12/00*   (2009.01)
(Continued)

(52) U.S. Cl.
CPC ............ *H04W 12/00* (2013.01); *G06F 9/455* (2013.01); *G06F 19/3406* (2013.01); *H04L 9/32* (2013.01); *H04L 67/12* (2013.01); *H04L 2209/88* (2013.01)

(58) Field of Classification Search
None
See application file for complete search history.

(56) References Cited

U.S. PATENT DOCUMENTS 5,602,917 A    2/1997  Mueller
5,764,159 A    6/1998  Neftel
(Continued)

FOREIGN PATENT DOCUMENTS

EP    0 720 326 A2    7/1996
EP    1 282 260 A1    2/2003
(Continued)

OTHER PUBLICATIONS

P. Gilbert, L. P. Cox, J. Jung, and D.Wetherall. Toward trustworthy mobile sensing. In Proc. Workshop on Mobile Computing Systems and Applications, 2010.*

(Continued)

*Primary Examiner* — Christopher Revak
*Assistant Examiner* — Vadim Savenkov
(74) *Attorney, Agent, or Firm* — Nixon & Vanderhye P.C.

(57) ABSTRACT

The invention concerns a medical assembly which insures a secured communication between a medical device (like a insulin pump) and its remote control which manages the medical device. To this effect, said assembly use an external microcontroller (MCU) which contains the secured data and uses a cryptographic mechanism to communicate with the medical device. One single external microcontroller (MCU) is paired with only one medical device in such a way the patient can change several times of remote device although aware that the remote device, in which said external protected MCU is inserted, is the single remote device paired with the medical device. In said assembly, said medical device and said external microcontroller (MCU) comprise secured memories which contain the wireless communica- (Continued)

tion configuration in such a way the devices know in advance the good configuration.

21 Claims, 10 Drawing Sheets

(51) Int. Cl.
  *H04L 29/08* (2006.01)
  *G06F 19/00* (2018.01)
  *G06F 9/455* (2018.01)

(56) References Cited

U.S. PATENT DOCUMENTS

| | | | |
|---|---|---|---|
| 7,856,103 B2* | 12/2010 | Kimura | H04L 9/3271 380/44 |
| 2003/0026428 A1 | 2/2003 | Loisel | |
| 2005/0204134 A1 | 9/2005 | Von Arx et al. | |
| 2006/0190726 A1 | 8/2006 | Brique et al. | |
| 2006/0200864 A1 | 9/2006 | Nakanishi et al. | |
| 2008/0140157 A1* | 6/2008 | Goetz | G06F 19/3406 607/59 |
| 2008/0140160 A1 | 6/2008 | Goetz et al. | |
| 2008/0285626 A1* | 11/2008 | Claus | H04W 12/06 375/133 |
| 2009/0058635 A1* | 3/2009 | LaLonde | A61N 1/37282 340/539.11 |
| 2009/0058636 A1 | 3/2009 | Gaskill et al. | |
| 2009/0254986 A1* | 10/2009 | Harris | G06F 21/74 726/17 |
| 2009/0307491 A1* | 12/2009 | Nakatsugawa | G06Q 20/341 713/169 |
| 2010/0045425 A1 | 2/2010 | Chivallier | |
| 2010/0115279 A1* | 5/2010 | Frikart | G06F 19/3406 713/171 |
| 2010/0185874 A1* | 7/2010 | Robles | G06F 21/6218 713/189 |
| 2010/0292556 A1* | 11/2010 | Golden | A61B 5/7465 600/364 |
| 2010/0318578 A1* | 12/2010 | Treu | G06F 19/3418 707/802 |
| 2011/0170692 A1* | 7/2011 | Konrad | H04L 9/002 380/260 |
| 2011/0197067 A1 | 8/2011 | Corndorf | |
| 2013/0141438 A1 | 6/2013 | Neftel | |
| 2014/0059677 A1* | 2/2014 | Urness | G06F 19/3406 726/21 |

FOREIGN PATENT DOCUMENTS

| | | |
|---|---|---|
| JP | 2006-146337 A | 6/2006 |
| JP | 2009-124429 A | 6/2009 |
| JP | 2009-530880 A | 8/2009 |
| JP | 2010-510586 A | 4/2010 |
| JP | 2011-521581 A | 7/2011 |
| WO | 2007/104755 A1 | 9/2007 |
| WO | 2008/021920 A2 | 2/2008 |
| WO | 2008/064053 A2 | 5/2008 |
| WO | 2009/141587 A1 | 11/2009 |
| WO | 2011/161577 A1 | 12/2011 |

OTHER PUBLICATIONS

International Preliminary Report on Patentability (IPRP) Chapter 1, issued Apr. 29, 2014 for applicant's PCT/IB2012/055917 filed on Oct. 26, 2012.
European Search Report dated Feb. 10, 2012—issued in corresponding European Patent Application No. EP 11187121 that corresponds to PCT/IB2012/055917 filed on Oct. 26, 2012.
Written Opinion of the priority European Application.
Tenderich A: "ADA Device Report: New 'Jewel Pump' is Best in Show," Diabetes Mine, Jun. 28, 2010, pp. 1-10, XP002669231.
Menezes, et al: "Handbook of Applied Cryptography, Passage," Jan. 1, 1997, Handbook of Applied Cryptography; [CRC Press Series on Discrete Mathematics and Its Applications], CRC Press Series on Discrete Mathematics and Its Applications, Boca Raton, FL, US, pp. 397-406, XP002398862.
Sorber et al., "Plug-n-trust: Practical trusted sensing for mHealth", Mobisys '12, Jun. 25, 2012, pp. 309-322, XP002692324.
"BITS: A Smartcard Protected Operating System", Communications of the ACM, vol. 37, No. 11, Nov. 1994, pp. 66-70, 94, XP000485634.
International Search Report for PCT/IB2012/055917, dated Feb. 20, 2013.
Written Opinion for PCT/IB2012/055917, dated Feb. 20, 2013.
Sorber et al., "Plug-n-trust: Practical trusted sensing for mHealth", *Mobisys '12*, Jun. 25, 2012, pp. 309-322.
"BITS: A Smartcard Protected Operating System", *Communications of the ACM*, vol. 37, No. 11, Nov. 1, 1994, pp. 66-70.
Liu, Jingwei, et al., "Hybrid Security Mechanisms for Wireless Body Area Networks," Second International Conference on Ubiquitous and Future Networks (ICUFN), Jun. 16, 2010, IEEE, pp. 98-103, XP031731567.
Menezes, A., et al., "Handbook of Applied Cryptography," Chapter 12, Key Establishment Protocols, Dec. 31, 1997, 54 pages, XP055119322.
Sorber, Jacob, et al., "Poster: Practical Trusted Computing for mHealth Sensing," MobiSys '11, Jun. 28-Jul. 1, 2011, pp. 405-406, XP058004611.
Notice of Reason(s) for Rejection dated May 23, 2017, issued in Japanese Patent Application No. 2015-521119 and English translation.
Notice of Reasons for Rejection dated May 30, 2017, issued in Japanese Patent Application No. 2014-537799 and English translation.
Nakamura, Yuichi, "Which is stronger? Security Duel Fedora vs. Vista, Part 3", Nikkei Linux, Japan, Nikkei BP Inc., Jul. 8, 2007, No. 9(7), pp. 38-43.
The First Office Action dated Aug. 3, 2016, issued in Chinese Patent Application No. 2012800522335, and English translation.
Notice of Reasons for Rejection dated Sep. 13, 2016, issued in Japanese Patent Application No. 2014-537799, and English translation.
Nakamura, Yuichi, "Which is stronger? Security Duel Fedora vs. Vista, Part 3," Nikkei Linux, Japan, Nikkei BP Inc., Jul. 8, 2007, No. 9(7), pp. 38-43.

\* cited by examiner

MOBILE VIRTUALIZATION PLATFORM FOR THE REMOTE CONTROL OF A MEDICAL DEVICE

This application is the U.S. national phase of International Application No. PCT/IB2012/055917 filed 26 Oct. 2012 which designated the U.S. and claims priority to EP Patent Application No. 11187121.6 filed 28 Oct. 2011 and EP Patent Application No. 12175498.0 filed 9 Jul. 2012, the entire contents of each of which are hereby incorporated by reference.

FIELD OF INVENTION

The present invention relates to the remote control of a medical device such as but not limited to a delivery device (e.g. insulin pump) and/or a wireless sensor (e.g. continuous glucose meter) and/or an implantable device and/or a sampling device.

STATE OF THE ART

A remote control is required for controlling some medical devices like an insulin pump that is light and small like a patch pump, because it could be very difficult for the patient to see the content of a display that would be located on the pump itself. Most of the pumps today use a dedicated proprietary remote control, which represents another device to carry with all the disadvantages that it could generate like:
  To find a pocket to put it in a safe place with a fast and easy access.
  To not forget your remote control
  To think about charging it or to have spare batteries
  To prevent its deterioration due to a fall or any "bad" external condition, like exposure to the sun or to sand.
One way to prevent the use of another specific device is to integrate the remote control functionality into an existing device that the patient should already carry with him, such as but not limited to blood glucose meter or a cell phone, which would have all the capabilities required for integrating the remote control features.

Using a cell phone for this purpose is very attractive but brings many security aspects that must be addressed before allowing its use for programming an insulin pump. Among the important security features that must be ensured are:
  Integrity of the data that are displayed to the user
  Integrity of the commands that are sent to the insulin pump
  Integrity and protection of the databases, which store the therapeutic parameters of the patient and the logs of the infusion history and the events.
  Pairing securely the medical device with its remote control.
  Responsiveness of the software at any time (eg: raising an alarm while another software has the focus, ability to process user requests while other tasks are overloading the resources like the MCU, etc).

GENERAL DESCRIPTION OF THE INVENTION

The present application claims the benefit of the priority of EP 11187121.6 filed on Oct. 28, 2011 in the name of Debiotech and the priority of EP 12175498.0 filed on Jul. 9, 2012 in the name of Debiotech, the entire disclosure of which is incorporated herein by reference.

The purpose of the invention is to offer a robust environment for securing the communication between a medical device and its remote control. In the present document, the expression "to secure the communication" has to be understood as all means used to ensure the data exchange between the remote control and the medical device is correct, said data has been sent by an authorized operator (e.g. patient also called user) using the correct device and correctly received. Said means may be the checking of the integrity of the data or of the application or operating system, an encryption process, a pairing process, the verification of the identity of the operator, . . . To this effect, the invention may comprise a medical assembly (comprising said medical device and its remote control) using a loopback process and/or said remote control (or an additional microcontroller belonging to the medical device) incorporating a virtualization platform and/or said assembly using an additional microcontroller (MCU), which is inserted into (alternately plugged in) the remote control, may contain the secured data and/or may use a cryptographic mechanism to communicate with said medical device. Using said three distinct means (MCU, Loopback, virtualization) permits to improve in a substantial way the security, but it's also possible to use just one or two of said means.

Said medical assembly may comprise a remote control which may manage and/or monitor at least one medical device such as but not limited to a delivery device and/or a wireless sensor and/or an implantable device and/or a sampling device and/or a blood glucose monitoring, . . .

Said medical device comprises a communication means permitting a wireless communication with a remote control, an internal secured memory which contains the key information to secured said communication. Said medical device is paired with only one microcontroller (MCU) which comprises a secured memory which also contains said key information. Said MCU is designed to be plugged in a remote control.

In one embodiment using an external microcontroller, said assembly suitable for establishing a secured communication between a medical device and a remote control comprises:
  A remote control which comprises:
    A communication means permitting a wireless communication with said medical device,
    A connecting means to plug an additional microcontroller (MCU);
    A display means (optionally),
    At least one input means,
    At least one processor which is connected to the communication means, the connecting means, (optionally the display means) and the input means;
  A medical device which comprises:
    A communication means permitting a wireless communication with said remote control,
    An internal secured memory;
  A MCU which may be connected to said remote control; said MCU further comprises a secured memory;
  Wherein at least one medical device is exclusively paired with only one MCU;
  Wherein the internal memory of said medical device and the secured memory of said MCU contain the key information to secure the communication.

In the present document, a microcontroller (MCU) may be an integrated chip which is inserted into the remote control or an external device which is plugged in the remote control. Typically, a MCU includes a CPU, RAM, some form of ROM, IO ports, and timers. Unlike a computer or a remote control, which includes other components, a microcontroller (MCU) is designed for very specific tasks, for example to control a particular system. As a result, the MCU can be simplified and reduced, which cuts down on production costs. Moreover, said MCU doesn't bring another CPU and memories which the OS (of the remote control) could use to improve the performance of the remote control but it brings other functionalities in particular more securities. The MCU and the CPU of the remote control are different and have different tasks. In this invention, the MCU is fully independent from the remote control in such a way the MCU may be used with different remote controls. Said MCU can be a Smart card, Sim card, SD Card such as SDIO card (Secure Digital Input Output) . . . In this document, we can use indifferently the following terms: external microcontroller or additional microcontroller or MCU.

In a preferred embodiment, said medical device and said MCU comprise secured memories containing the wireless communication configuration. In such a way, said device and said MCU know in advance the good configuration. In particular, said MCU can contain the key information used to connect the remote control to the medical device and to protect said communication.

Thus, said MCU is paired with only one medical device and said MCU is inserted into a remote control; In such a way, only the remote control containing said MCU can manage and/or monitor said medical device. Also, the patient can change remote control while knowing that the remote control, in which said MCU is inserted, is the single remote control that can manage and/or monitor the medical device.

In another embodiment, the remote control manages and/or monitors at least two medical devices. In this case, said two medical devices may be paired with only one MCU, alternatively each medical device is paired with its own MCU.

In one embodiment, said MCU contains the key information to connect said medical assembly with a medical server. In this embodiment, the medical assembly may use the data communication means of the remote control. Thus, said MCU may contain all information to secure the communication between the medical assembly and the medical server such as but not limited to the user authentication, the encryption parameters, . . .

In one embodiment, the MCU may store in the secured memory at least a set of data sent by the medical device or other set of data provided from the remote device or other devices. In another embodiment, said data are encrypted and stored in the remote device or medical device but only the MCU (or medical device) contains the key to decrypt said data.

In one embodiment in which remote control uses a virtual platform, the remote control incorporates a virtualization platform comprising:
  a host operating system (hOS) emulating hardware components for at least one guest operating system (gOS),
  a first gOS handling common functions such as but not limited to calendar or contacts, all those common functions being designed to be used in an uncontrolled environment,
  a medical operating system (mOS) handling remote control functions for a medical device, all those remote control functions being designed to be used in a controlled environment. Said mOS may be a specific gOS.

In the present document, the expression "host operating system" has to be understood as an operating system as thin as possible such as an enhanced hypervisor which is alone to manage and to share all remote control peripherals such as RAM, Flash, UART, Wifi, . . . The hOS doesn't handle common functions, its purpose is to secure the commands sent to the medical device.

In one embodiment, a MCU (like discovered above) is plugged in the remote control, but said host operating system can't manage and share the peripherals of said MCU.

In a preferred embodiment, said hOS is more than a standard hypervisor. Said hOS, although being as thin as possible, contains some operating process(es) to deny some application (running in the uncontrolled environment or controlled environment) or give some priorities.

In the present document, the expression "guest operating system" has to be understood as a standard operating system (such as but not limited to Android, iOS from Apple, . . . ) which handles the common functions (phoning, sending data, calendar, . . . ) or a specific operating system (such as a medical operating system). Said distinct guest operating systemes may co-exist on the same remote control in strong isolation from each other.

In the present document, the expression "controlled environment" has to be understood as a space where:
  the responsiveness of the intended application is deterministic
  the list and version of the software packages and the operating system are known and can't be changed by the users
  the access to the hardware components is controlled and guaranteed
  the responsiveness of the hardware components (CPU, memory, RF link, etc) is deterministic
  a predefined minimum bandwidth is always garanteed to access hardware components (eg: CPU, network RF link, etc)
  at least one medical application and/or mOS is run and stored The controlled and uncontrolled environments are totally isolated.

As a consequence, the uncontrolled environment has no visibility on the interactions between the hardware and the controlled environment. Advantageously, the guest operating system or the applications which are in the controlled environment (such as but not limited to the medical operating system and/or the medical application) has priority over another. Thereby, the host operating system decides to block an application running in the uncontrolled environment in order to avoid any perturbation caused by this application. The host operating system may also decide which application from the controlled or the uncontrolled environment will take the focus on the screen.

In one embodiment, the remote control according to the invention is a cell phone. Any suitable OS can be used, for instance Android. The remote control is used in combination with a medical device. Advantageously, the remote control functions are designed for the remote control of an insulin pump.

In one embodiment using an external MCU, said MCU is also used to authenticate and ensure the integrity of hOs.

In one embodiment of a medical assembly, said assembly advantageously comprises a loopback mechanism between both objects (e.g. insulin pump and remote control).

In the present document, the loopback mechanism isn't a simple confirmation of the data entered by the user. The loopback mechanism permits to confirm the data received by the medical device. So, the user enters the command (with the input means) and sends it to the medical device via a secured communication. Thanks to said mechanism, before launched the command, the medical device has to ask a confirmation if the received command is the command sent by him. When, the user confirms to the medical device, the command is launched. Advantageously, to improve the security, the user has to enter a PIN Code to confirm the command.

The security of the loopback mechanism and the connectivity to the medical device can be advantageously protected by using an additional protected MCU into the remote control, like a smart card or a SIM or SD Card . . .

The present invention offers in particular the following advantages:

- The invention also provides a controlled environment in which the responsiveness, the integrity and the security are ensured by the core design of the low level operating system architecture.
- The proposed solution provides a secured environment, which may for instance prevent any unwanted application that could mimic the normal use by changing the therapy, like programming several additional infusions not wanted by the patient.
- Using a MCU, which is independent of remote control as a smart card, permits to connect automatically and securely the remote control with the medical device without to be visible by another device during the pairing process.
- Using a MCU, which may be inserted into or plugged in different remote controls like a cell phone, permits to change of remote control in case of problem (low battery, forgetting or losing the remote control, . . . ).
- Using a loopback process permits to ensure that the value programmed in the medical device (for instance an insulin pump) corresponds to the value expected by the user on the remote control.
- At the end of the loopback process, the user acknowledges the value preferably by entering a PIN code (which only the user knows) on the remote control. Using said PIN code ensures the confirmation is approved by the correct user.
- Using the virtual platform ensures the medical application or mOS is priority and securely run.
- The hOS ensures some peripherals (MCU, LED, part of the screen, vibrator, . . . ) are only used by the medical application and/or mOS.

LIST OF FIGURES

The invention is discussed below in a more detailed way with examples illustrated by the following figures.

Figure 1:
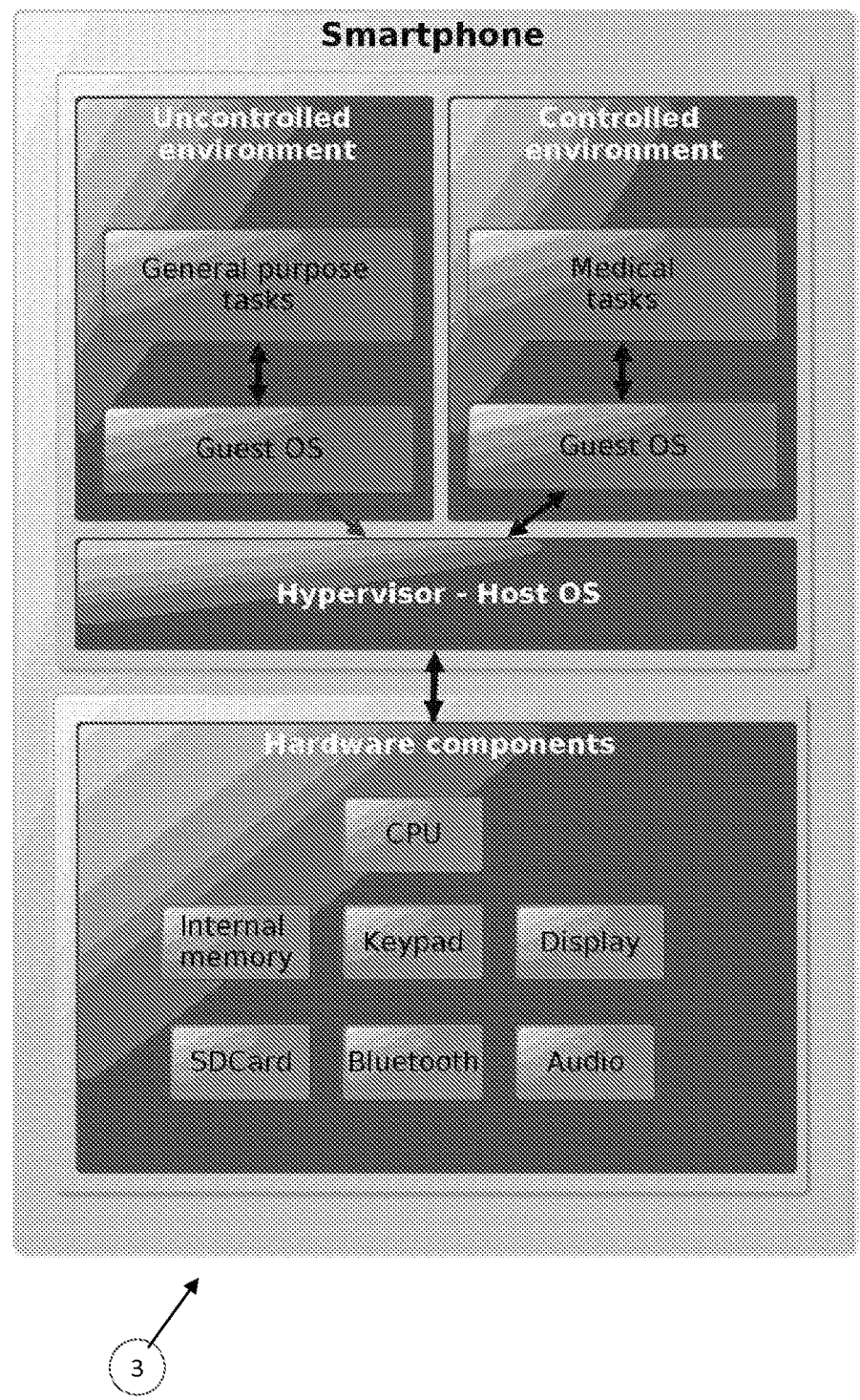
FIG. 1 shows the display of a remote control (3) according to the invention, which includes a virtualization platform.

LIST OF COMPONENTS 1 a medical device
2 wireless communication
3 remote control
4, 4a, 4b, 4c a microcontroller (such as a smart car)
5 secured processing means
6 another type of microcontroller
7 another medical device

DETAILED DESCRIPTION OF THE INVENTION

Using an Additional Microcontroller (MCU)

In a preferred but not limited to embodiment as is shown in FIGS. 5 to 10, a medical assembly suitable for establishing a secured communication between a medical device (1, 7) and a remote control (3) comprising:

A remote control (3) which comprises:
  A communication means permitting a wireless communication (2) with said medical device (1, 7),
  A connecting means to plug an additional microcontroller (MCU) (4, 6);
  A display means (optionally),
  At least one input means,
  At least one processor which is connected to the communication means, the connecting means, the display means and the input means;
A medical device (1, 7) which comprises:
  A communication means permitting a wireless communication (2) with said remote control (3),
  An internal secured memory;
  An MCU (4, 4a, 4b, 4c, 6) which may be connected to said remote control (3); said MCU (4, 4a, 4b, 4c, 6) further comprises a secured memory;

Wherein at least one medical device (1, 7) is exclusively paired with only one MCU (4, 4a, 4b, 4c, 6);

Wherein the internal memory of said medical device (1, 7) and the secured memory of said MCU (4, 4a, 4b, 4c, 6) contain the key information to secure the communication.

Said medical device (1, 7) may be a delivery device (such as but not limited to an insulin pump) and/or a wireless sensor (which may measure physiological properties of the patient.) and/or an implantable device and/or a sampling device The processor of the remote control (3) is the main computing unit of the remote control. It is the one running the remote control operating system (OS) (or operating systemes OSes), and has access to all the remote control (3) peripherals such as RAM, Flash, UART, Wifi, etc.

The MCU (4, 4a, 4b, 4c, 6) contains also a processor as well, which runs its own operating system and code. That processor however has only access to the internal peripherals of the MCU (4, 4a, 4b, 4c, 6) (crypto engine, communication interface, etc.). The processor of the MCU (4, 4a, 4b, 4c, 6) (such as but not limited to a smart card) has no access to the peripherals of the remote control (3). The only interaction between the two devices (MCU (4, 4a, 4b, 4c, 6) and remote control (3)) is via a communication link. Thus, the processor of the remote control (3) and the processor of the MCU (4, 4a, 4b, 4c, 6) are independent of each other. Thus, said MCU (4, 4a, 4b, 4c, 6) can be plugged in distinct remote control and ensure a total security.

In one embodiment, the remote control (3) also has another processor in the form of the BGM (blood glucose monitor) module. However it only interacts with the remote control (3) via a communication link.

Figure 5:
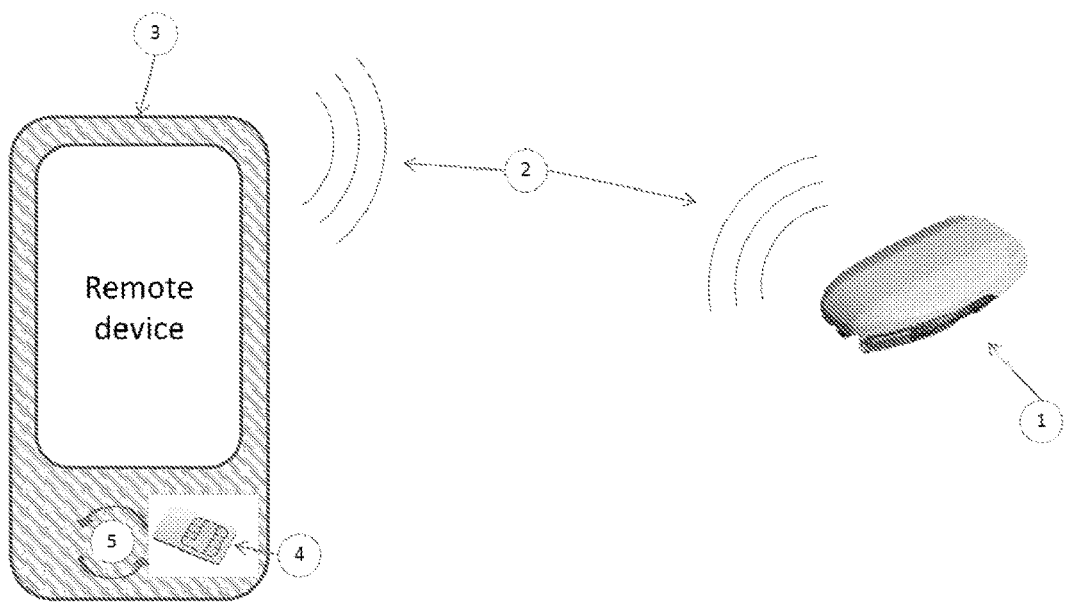
FIG. 5 shows a medical device (1) communicating with a remote control (3) which comprises inside a MCU such as a Smart Card (4)

In one embodiment as is shown in FIG. 5, the medical device (1) communicates with a remote control (3). Said remote control (3) comprises inside a MCU (4) (such as but not limited to a smart card or a SIM card) which is only paired with said medical device (1). The communication (2) between said remote control (3) and said medical device (1) is securised thanks to the secured processing means (5) launched or executed by said smart card (4).

In one embodiment, the remote control (3) is a cell phone and the MCU (4) is a sim card which includes all data and applications of the telephone operator and all data and applications to pair and to communicate securely with the medical device (1, 7). In one embodiment, said remote control (3) comprises a virtualization platform as is disclosed thereafter. In a another embodiment, said cell phone comprises two distinct connecting means, the first one to plug the SIM Card of the telecom operator and the another to plug the MCU paired with the medical device.

In one embodiment, said MCU (4, 4a, 4b, 4c, 6) contains the key information to secure communication between said medical assembly and a medical server (e.g. telemedicine). In such a way, some data may be securely send to the medical server where said data may be analysed or stored.

Figure 6:
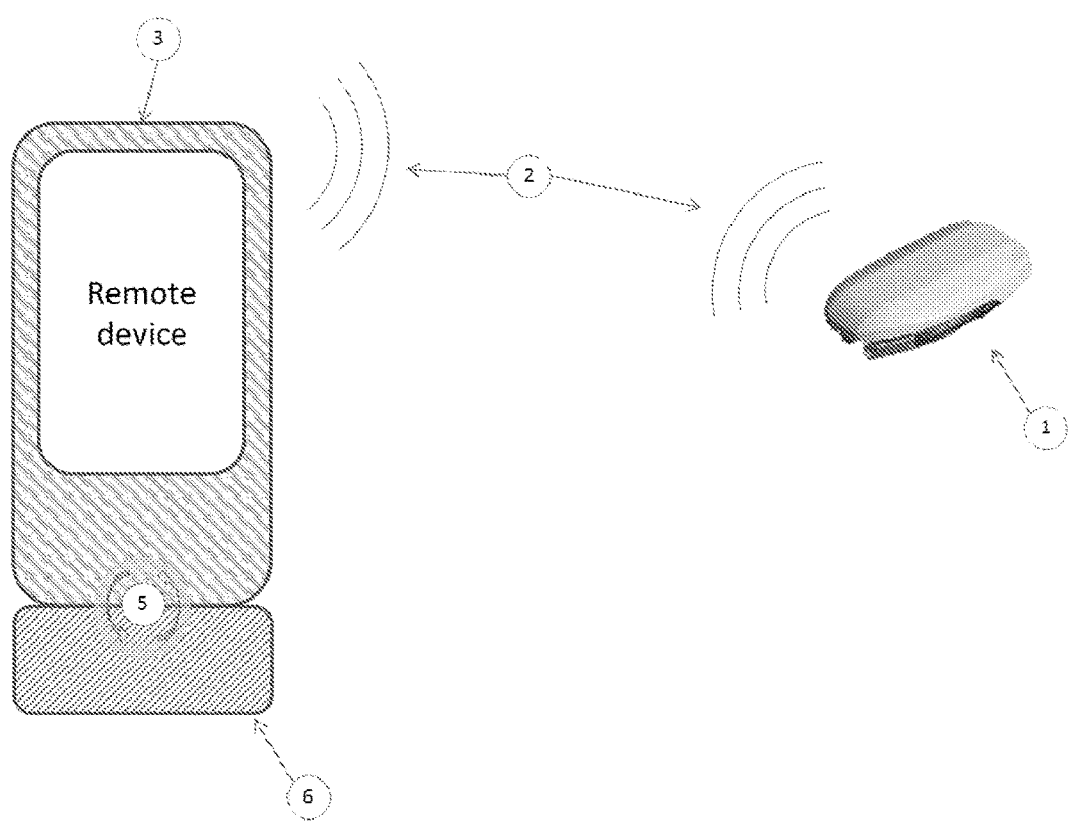
FIG. 6 shows a medical device (1) communicating with a remote control (3) plugged to an MCU (6)

In one embodiment as is shown in FIG. 6, the medical device (1) communicates with a remote control (3). Said remote control (3) is plugged in an MCU (6) which is only paired with said medical device (1). The communication (2) between said remote control (3) and said medical device (1) is secured thanks to the secured processing means (5) launched or executed by said MCU (6).

In one embodiment, the MCU (6) may be considered as or be an external device comprising all precedent elements and other means. For example, said MCU (6) may comprise a sensor, such as but not limited to, a blood glucose measuring means in such a way, said MCU (6) may be also used like blood glucose monitoring.

In one embodiment, said MCU (6) may comprise communication means to communicate securely with the medical device without depending of the remote control. In this embodiment, the remote control, which may be a mobile phone, is used advantageously for its display means.

Figure 7:
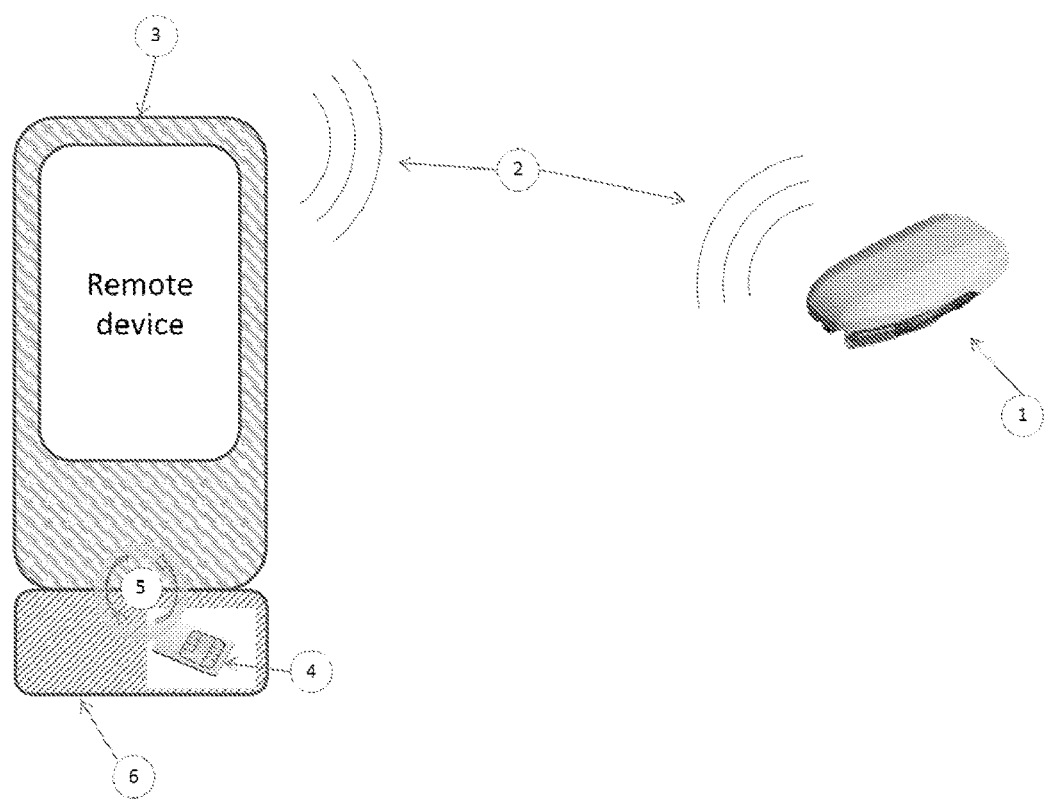
FIG. 7 shows a medical device (1) communicating with a remote control (3) plugged to an MCU (6) which comprises inside another MCU such as a Smart Card (4)

In one embodiment as is shown in FIG. 7, the medical device (1) communicates with a remote control (3). Said remote control (3) is plugged to a first MCU (6) which comprises inside a second MCU (4) (like a smart card or sim card). Said second MCU (4) is only paired with said medical device (1). The communication (2) between said remote control (3) and said medical device (1) is secured thanks to the secured processing means (5) launched or executed by said first MCU (6) and or said second MCU (4). In one embodiment, said MCU (6) comprises sensor, such as but not limited to, a blood glucose measuring means in such a way, said MCU (6) may be also used like blood glucose monitoring.

Figure 8:
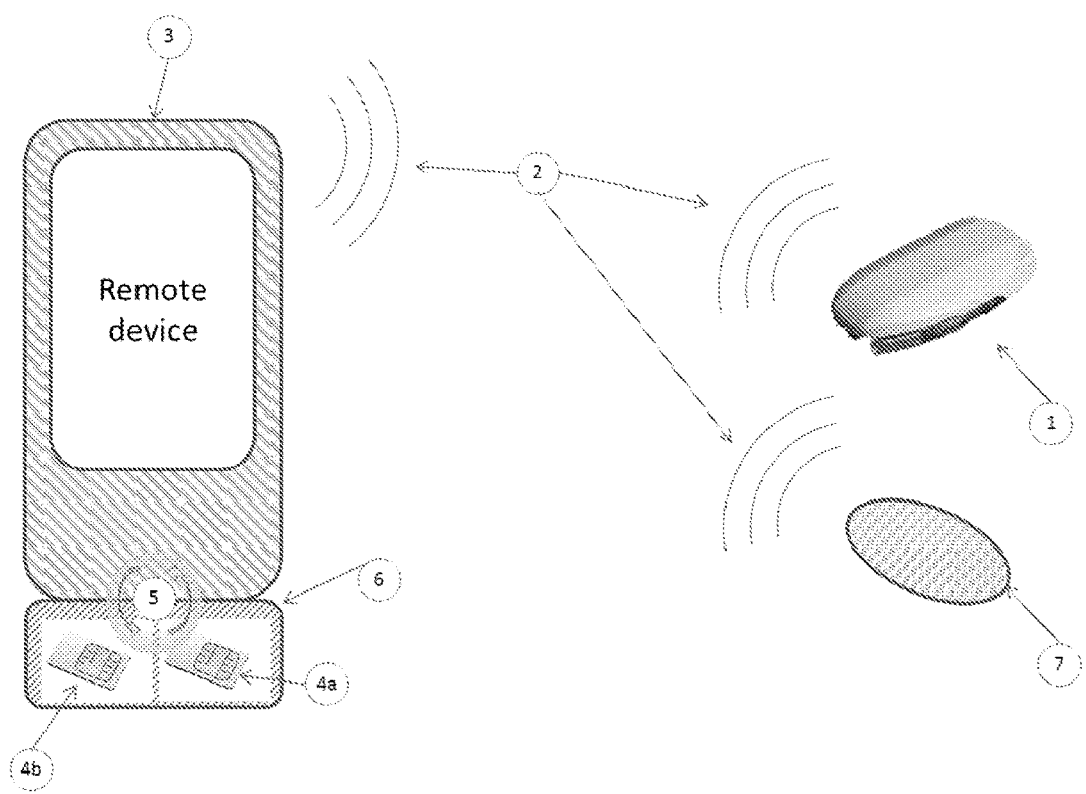
FIG. 8 shows two medical devices (1, 7) communicating with a remote control (3) plugged to an MCU (6) which comprises inside two MCU such as Smart Cards (4a, 4b)
Figure 9:
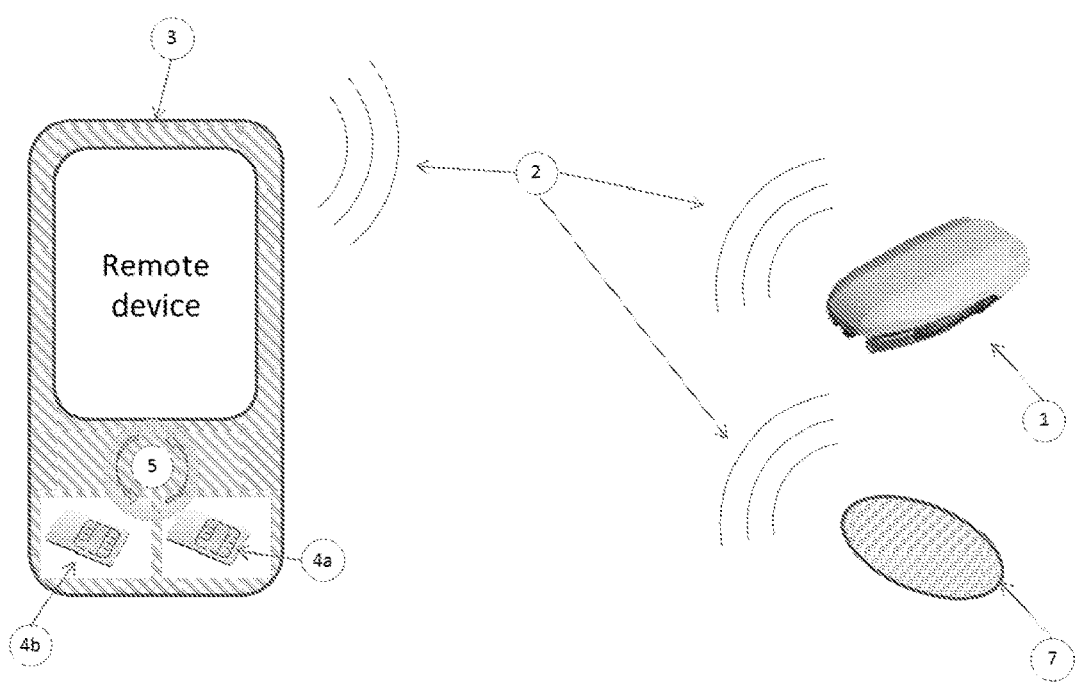
FIG. 9 shows two medical devices (1, 7) communicating with a remote control (3) which comprises inside two MCU such as Smart Cards (4a, 4b)

In one embodiment as is shown in FIGS. 8 and 9, two medical devices (1, 7) communicate with a remote control (3). For example, the first medical device (1) is an insulin pump (1) and the second medical device (7) is a continuous blood glucose meter (7). Each medical device is only paired with its own MCU (4a, 4b). The embodiment as is shown in FIG. 8 discloses a remote control (3) plugged to a first MCU (6). Said first MCU (6) comprises two different connection means to insert a second and a third MCU (4a, 4b). The embodiment as is shown in FIG. 9 discloses a remote control (3) comprising inside two different connections means to insert two distinct MCU (4a, 4b) without needing the first MCU (6). The second MCU (4a) (respectively, the third MCU (4b)) comprises a secured memory containing the wireless communication (2) configuration with the first medical device (1) (respectively, the second medical device (7)). Said second MCU (4a) is only paired with the first medical device (1) and said third MCU (4b) is only paired with the second medical device (7). The embodiment may comprise more MCU and medical device.

Figure 10:
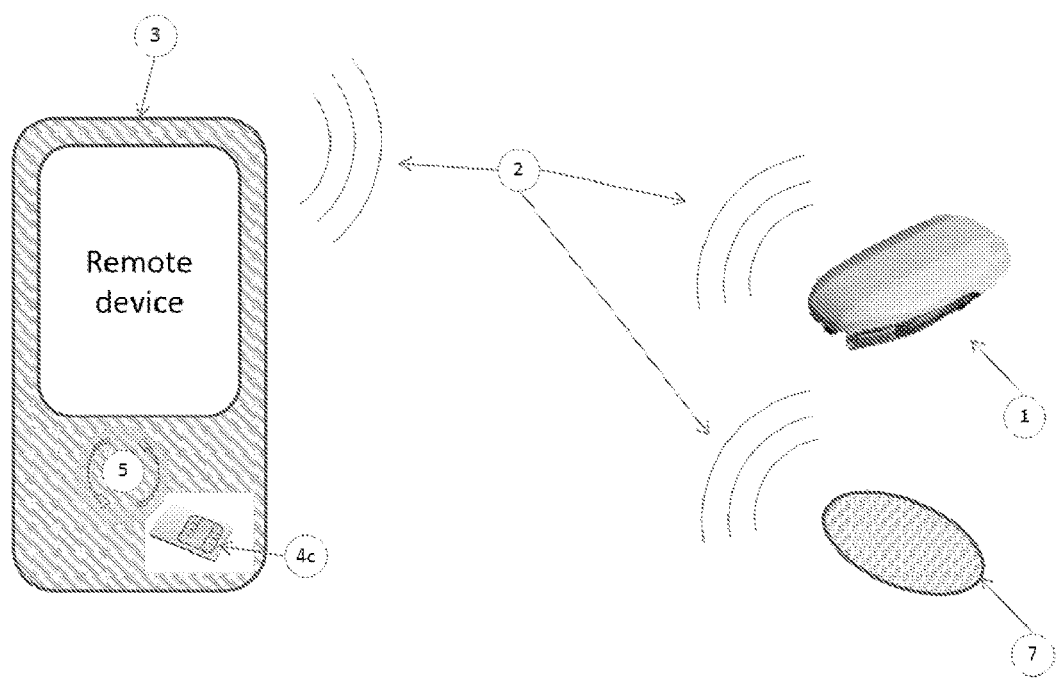
FIG. 10 shows two medical devices (1, 7) communicating with a remote control (3) which comprises inside a single MCU such as a Smart Card (4c)

In one embodiment as is shown in FIG. 10, two medical devices (1, 7) communicate with a remote control (3) but only one MCU (4c) is plugged. For this embodiment, said MCU (4c) is paired with said two medical devices (1, 7) and comprises at least one secured memory containing the wireless communication (2) configuration with said two medical devices (1, 7).

Although, the embodiments described above use one or two medical device, the invention isn't limited to that embodiment, the invention can have one or more medical device and one or more MCU.

In one embodiment, the pairing may be directly executed prior to sale (for example at the factory) or before to plug the MCU (4, 4a, 4b, 4c, 6) in the remote control (3). In one embodiment, said MCU and/or medical device can't accept a new pairing request.

In one embodiment, said medical device (1, 7) and/or said MCU (4, 4a, 4b, 4c, 6) comprise secured processing means (5), such as secure boot process and/or secure flash process and/or a cryptographic mechanism, which check at least the integrity of the remote control and/or manage a secured communication (2) of data between said medical device (1, 7) and said remote control (3).

Thus, said MCU (4, 4a, 4b, 4c, 6) may be used to ensure the integrity of the remote control (3), such as but not limited to its operating system and/or hOs and/or applications, . . . Typical way to ensure this integrity is to use a secure boot or a secure flash, which is a function that performs an integrity check during the boot of the remote control (3) or at regular interval via a monitoring system.

For example, an embodiment using the secure boot process: in order to ensure that the software running on the remote control (3) has not been modified, either by accident (hardware failure) or intentionally (attacker, malware), a mechanism of secure boot is used. When the remote control (3) is turned on, the first code executed by its processor is a routine that will compute a signature of the contents of the remote control (3) internal storage (Flash memory), and verify the validity of this signature. Once the signature has been verified as valid, that processor continues with its normal OS startup procedure.

Otherwise, the system does not start up. It's important to note the verification of the signature is performed using the MCU (4, 4a, 4b, 4c, 6), which ensures that no secrets (keys) are exposed.

Another example, an embodiment using the secure flash process: we wish to allow the user to take advantage of newer versions of the remote control OS. Similarly, in order to prevent the software of the remote control (3) to be updated with unauthorized software, the new software to be written must be signed. When the remote control (3) is started in update mode (with a long press on the power button, for example), the processor executes first a routine that will download the image of the new software, compute its signature and verify it, before overwriting the existing software. Again, it's important to note the verification of the signature is performed using the MCU (4, 4a, 4b, 4c, 6), which ensures that no secrets (keys) are exposed.

Thus, in one embodiment shown above, the presence of said MCU (4, 4a, 4b, 4c, 6) avoids the replacement of the hOs by a corrupted software.

In one embodiment, the MCU (4, 4a, 4b, 4c, 6) may also contain key information (such as but not limited to: communication configuration, public key, private key, cryptography process, . . . ) which allows the wireless connection to the medical device (1, 7) which also knows partially or integrally said key information. Without said key information, it is not possible to connect to the medical device (1, 7). This feature can be illustrated by using a Bluetooth communication where the medical device (1, 7) will never be discoverable. The remote control (3) needs the link key to initiate a Bluetooth connection without using the standard pairing process. In this particular case, the link key can be read into the MCU (4, 4a, 4b, 4c, 6) and then transferred to the Bluetooth communication layer, which can request straight the connection.

In one embodiment, said secured processing means (5) may use:
an asymmetric key cryptography mechanism generating at least one asymmetric key pair and/or symmetric key;
a symmetric key cryptography mechanism generating at least one symmetric key and/or asymmetric key
a cryptographic hash mechanism.

Said asymmetric key cryptography mechanism may use at least one of this algorithm: Benaloh, Blum-Goldwasser, Cayley-Purser, CEILIDH, Cramer-Shoup, Damgard-Jurik, DH, DSA, EPOC, ECDH, ECDSA, EKE, ElGamal, GMR, Goldwasser-Micali, HFE, IES, Lamport, McEliece, Merkle-Hellman, MQV, Naccache-Stern, NTRUEncrypt, NTRU-Sign, Paillier, Rabin, RSA, Okamoto-Uchiyama, Schnorr, Schmidt-Samoa, SPEKE, SRP, STS, Three-pass protocol or XTR.

In one embodiment, the secured memory of said MCU contains a private key and the secured internal secured memory of said medical device contains the appropriate public key.

The pairing between the remote control (3) and the medical device comprises the following steps:
Inserting said MCU (4, 4a, 4b, 4c, 6) in the remote control (3),
Said MCU (4, 4a, 4b, 4c, 6) uses the wireless communication configuration (contained in the secured memory of said MCU (4, 4a, 4b, 4c, 6)) to connect the medical device with the remote control (3),
Said medical device (1, 7) uses said wireless communication configuration (contained in the secured memory of said medical device (1, 7)) to be connected with the remote control (3),
Advantageously, said MCU (4, 4a, 4b, 4c, 6) and said medical device (1, 7) use a cryptographic mechanism to authenticate the connection.

Thus, the medical device (1, 7) and the remote (3) don't use the standard pairing process which forces the medical device (1, 7) to be visible to other devices.

In one embodiment, the MCU (4, 4a, 4b, 4c, 6) keeps in its secured memory said secured processing means (5) in such a way that said remote control (3) does not access to said secured processing means (5).

In one embodiment, the medical device also comprises said secured processing means that manages the encrypted communication of data between the secured memory of medical device and the remote device.

Using a Host Operating System (hOS)

In a preferred but not limited to embodiment, attention is now directed to FIG. 1, the remote control (3) use of a mobile virtualization platform offers the possibility to divide the remote control (3) (e.g. a smartphone) into a controlled environment (e.g. for controlling the medical device (1, 7)) and an uncontrolled environment (e.g. for general purpose tasks). The virtualization platform can be defined via a virtual machine application.

The architecture below describes a non-limiting example of a virtualization platform according to the invention (see FIG. 1):
a host Operating System (OS) emulating the hardware components to one or several guest OS (only 2 guest OS are illustrated on FIG. 1).
one guest OS handling the general purpose tasks (eg: calendar, contacts, web browsing, phone communication, entertainment, etc) in an uncontrolled environment
one guest OS handling the interaction with the medical device in a controlled environment Advantageously, the hOS is as thin as possible while integrating some advance operating processes and is in the lowest level operating system architecture. The host operating system isn't a simple hypervisor. Indeed, the host operating system further contains different security tasks and control tasks. Thus, the host operating system manages, coordinates the activities, shares the resources of the remote control and decides to deny and/or admit running application and/or using driver and/or peripherals of the remote control (3). In such a way the security is improved because a malicious software can't access any drivers and/or peripherals, such as but not limited to the MCU like described above.

Thus, by using this architecture, the controlled environment has always the full control of the remote control in order to prevent any malicious application either to intercept or to modify or to generate commands/information exchanged with the medical device. A typical action of such a malicious application would be to steal the PIN code of the user in order to mimic the programming of an infusion.

In one embodiment, this controlled environment is authenticated and its integrity is checked by means of an MCU as described above. At any boot of the Remote Control a safe check is done via said MCU, which shall confirm the integrity and authenticate the hOs and optionally the mOS.

In addition to this architecture, a specific monitoring program can be implemented to check all running tasks in the controlled environment, which can disable any application that is not within a specific list of authorized applications. This specific monitoring can also be controlled by means of said MCU. Said monitor may also be able to measure the running time used by the application and indicate to the user any suspect overload of activity by triggering an alarm.

In one embodiment, said hOS is containing in and/or launching and/or running by said MCU.

In one embodiment, said mOS is containing in and/or launching and/or running by said MCU.

In one embodiment, said mOS and/or said hOS is containing in said MCU. When said MCU is inserted into the remote control, the MCU installs on the remote control said mOS and/or hOS.

In one embodiment, the processing in the controlled environment can be signalled by using a visual indicator and/or audio indicator and/or other indicator (such as a vibrator), like a LED, which will signal to the user the fact that the current application is running in the controlled or not controlled environment. By example, we can imagine that a green LED will be switched ON when the current application is in the controlled environment and then, will be switched OFF when user returns in the not controlled environment. We could also have an "opposite" use case where the LED in OFF when user is in the controlled environment and becomes red when user returns in the uncontrolled environment.

In another embodiment, the hOS may reserve a part of the screen to the application running in controlled environement. In such a way, only the mOS can display something in this space and the application or other gOS, which is run in uncontrolled environment, can't use this space.

Thus, the user knows that the application of the mOS is running or not. Indeed, if said indicator doesn't inform the user correctly, it's certainly a malicious application which attempts to take the control of the medical device or attempts to mislead the user.

Using a Loopback Mechanism

Figure 3:
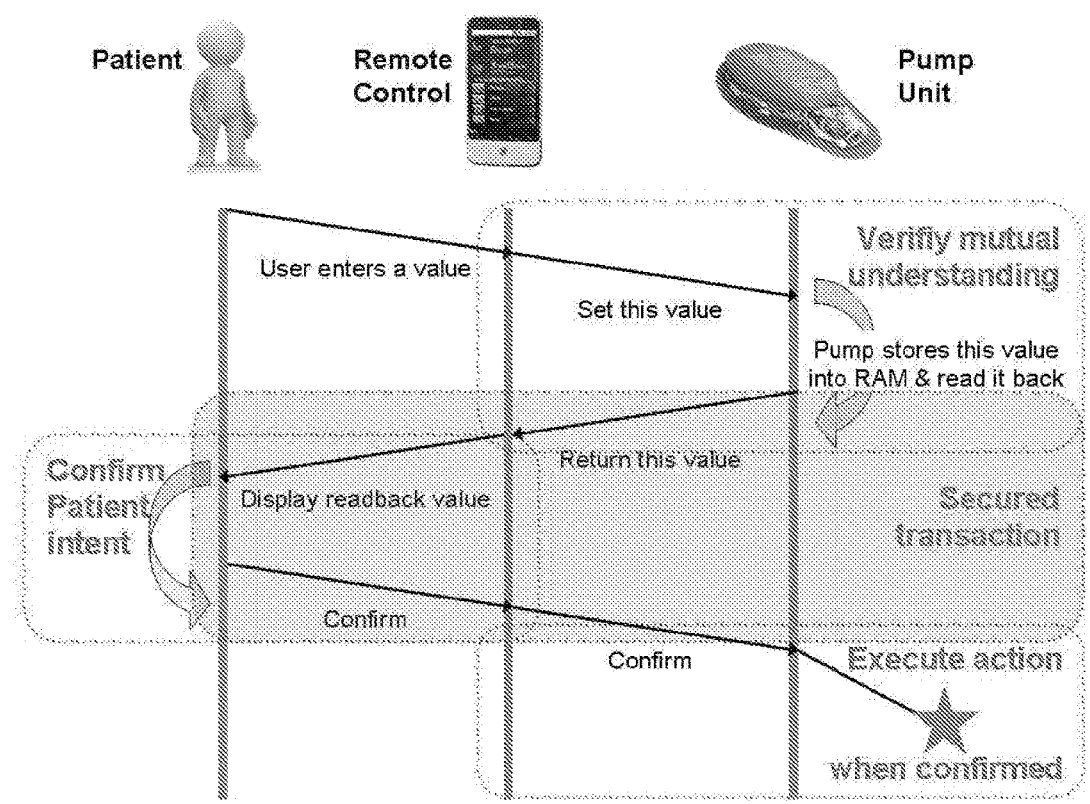
FIG. 3 illustrates a loopback mechanism according to the invention
Figure 4:
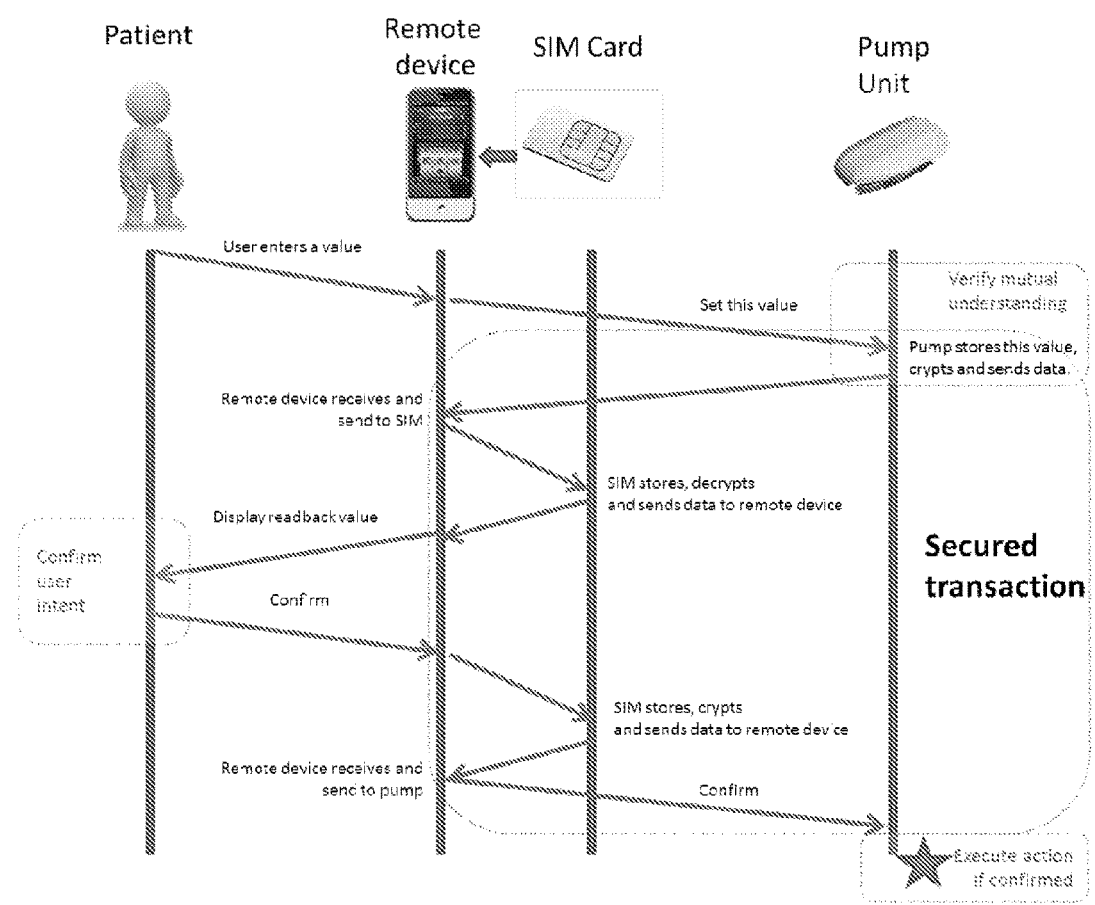
FIG. 4 illustrates a loopback mechanism according to the invention using a MCU.

The next paragraphs relate to a preferred embodiment of the invention which comprises a loopback mechanism. This feature may provide a secure communication between the medical device and the remote control, by taking into account that the architecture disclosed previously or a similar level of security is provided inside the remote control in order to ensure a secured bridge between the assembly according to the invention and the information read or entered by the patient. FIGS. 3 and 4 illustrate the use of a loopback mechanism with the remote control (3) according to the invention.

The loopback is a mechanism that ensures that a command executed on the medical device (1, 7), along with its parameters, has been requested by the operator (authentication) and corresponds to his wishes (integrity). More precisely, the mechanism first ensures that the information transmitted between the remote control (3) and the medical device (1, 7) is not altered, either by accident (memory failure, communication interferences), or voluntarily (attacker, malware). Furthermore, the mechanism ensures that the command has indeed been requested by the user. These two functions are accomplished by the following tasks such as but not limited to:

The commands, along with its parameters, are transmitted by the remote control (3) to the medical device (1, 7).

The medical device (1, 7) generates a challenge based on the command and its parameters, and returns it to the remote control (3).

The remote control (3) extracts information from the challenge and displays it to the user for confirmation. This information includes the command and its parameters as received by the medical device (1, 7).

The user signals his approval and confirmation by entering a PIN known only by him. The remote control (3) generates the response to the challenge using the PIN and the challenge itself.

The response is transmitted to the medical device (1, 7) and verified by it. The command actually starts executing only if the challenge's response is correct.

This mechanism differs from a standard "login" mechanism, in the sense that the PIN used by the user validates only for the particular instance of challenge-response. In such a way, each command has to be validated by the user, thus a malicious application can't send a new command right after the user has entered the PIN Code. Furthermore, another person can't send a command with the correct remote control or other device by mistake or intentionally because the user is the only person to know the PIN code.

It differs also from just repeating the requested command to the user with a "Are you sure?" mechanism, in the sense that the information showed to the user and for which his approval is requested is information returned by the target device. If any alteration has taken place, this returned value will automatically differ from the information originally entered by the user.

Said confirmation isn't automatically handled by the remote device so that a malicious application can't control said confirmation. It is essential that the confirmation is permitted only by the user who knows the PIN code to confirm the command sent.

Preferably a direct secured pipe is created between the memory of the medical device and a secured buffer on the remote control, which contains the displayed values. Then an authorized application on the remote control (3) displays the value and records a user authentication, which will be used to construct the return value, which is sent back to the medical device. This secured pipe can be initiated by using information that is inside the additional MCU.

The secured pipe is open when the user has finished defining the parameters that he wants to program on the medical device. It is closed when the user has acknowledged the parameters in order to allow the medical device using them.

The loopback process according to the present invention preferably requires the implementation of the following elements:

A secured memory area in the medical device

A secured process in the medical device that manages the encrypted communication of data between the secured memory area of the medical device to the remote control.

A secured display memory area in the remote control

A secured process on the remote control that manages the encrypted communication of data between the medical device to the secured display memory area of the remote control.

A secured and authorized process on the remote control that transfers the data from the secured display memory area to the display of the remote control and builds the acknowledgement ticket of the user.

Figure 2:
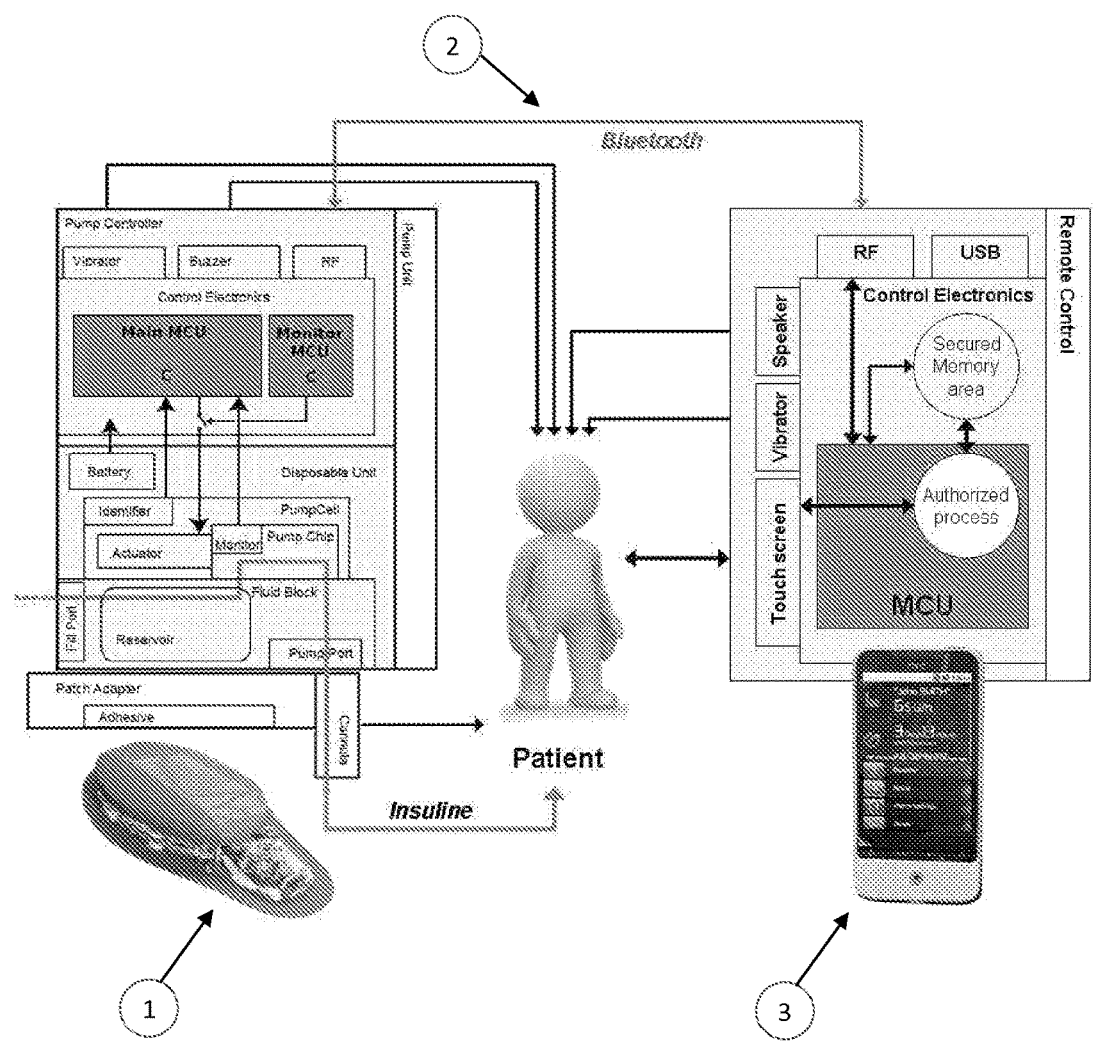
FIG. 2 shows the overall architecture of a preferred embodiment of the invention, namely an assembly comprising a remote control (3) and a medical device (1).

The architecture of these different elements is illustrated in FIG. 2.

The loopback process is initiated when the medical device has received a set of parameters, which will change the set-up of the therapy or any security feature like the alarm settings.

In one embodiment which doesn't use an additional MCU, an medical assembly (at least one medical device and one remote control) comprises:

a memory in said medical device which may contain a secured memory area, secured processing means (5) in said medical device that manages the encrypted communication of data between said secured memory area and the remote device, a secured memory area in the remote control, secured processing means (5) in the remote control that manages the encrypted communication of data between the medical device and said memory area, secured and authorized processing means (5) on the remote control that transfers the data from the secured memory area to the display of the remote control and builds the acknowledgement ticket of the user.

The process preferably comprises the following steps:

Done by the embedded software in the medical device
- Write the parameters that must be acknowledged in the memory of the medical device
- Generate a random information, commonly named a challenge
- Open a secure pipe between the medical device and the remote control
- Indicate to the user that the medical device and remote control is in loopback mode by means such as a vibration, sound, LED or any other method that informs the patient.
- Send the parameters encrypted by using an encryption key called KP and the challenge to the remote control.

Done by the software entity 1 in the remote control
- Receive and write the encrypted parameters and the challenge to the secured memory area of the remote control.

Done by the software entity 2 in the remote control
- Decrypt the parameters by using the key called KRC, which is the corresponding key to KP. These keys can be symmetric or asymmetric. The authorized application is validated by having the correct corresponding key KRC.
- Display the decrypted parameters in a "Summary" page.
- Enter the PIN code of the user.
- Build the acknowledgement ticket that will confirm the acceptance of these parameters by using the challenge, the key KRC and the entered PIN code.
- Write the ticket in secured memory area of the remote control.

Done by the software entity 1 in the remote control
- Send this ticket back to the medical device.

Done by the embedded software in the medical device
- Calculate the expected ticket
- Receive and validate the acknowledgement ticket coming from the remote control.

This process is illustrated in the FIG. 3. When the ticket is validated the loopback process is closed and the medical device is allowed to use the updated parameters. This basic process can be more elaborated or part of a more complex scheme in order to improve the security of the secured pipe.

In one embodiment, the PIN may be entered while using a random array display on the remote control device in order to prevent any application that would mimic user actions or intercept this information. For example, the numbers (5 from 0 to 9) would be displayed in a random order which would be different every time a PIN code shall be entered by the user.

In another embodiment, the PIN can be changed by another authentication means such as but not limited to fingerprint readers, fingerprint retinal, . . . The authentication means must be known or owned only to the user.

In one embodiment, said software entity 1 and said software entity 2 are the same software entity or software entity 1 may be embedded software in the remote control (3) and software entity 2 may be an authorized application in the remote control (3). In another embodiment, said software entity 1 is running by the host Operating System as defined above and the software entity 2 is running by the medical Operating System as described above.

One of skill in the art will appreciate that there are several ways to encrypt the data send and to generate said ticket. The invention is not limited to a particular way to encrypt the data send or to generate said ticket.

In one embodiment which includes the additional MCU, the process preferably comprises the following steps:

Done by the embedded software in the medical device:
- Write the parameters that must be acknowledge in the memory in the medical device
- Generate a challenge
- Encrypt said parameters by using a temporary key Ks1
- Indicate to the user that the medical device and remote control is in loopback mode by means such as a vibration, sound, LED or any other method that informs the patient.
- Send the encrypted parameters to the remote control Done by the embedded software in the remote control
- Send the encrypted parameters to the MCU.

Done by the embedded software in the MCU
- Receive and write the encrypted parameters and the challenge to the secured memory area of the MCU.
- Decrypt the parameters by using the key Ks1.
- Send the decrypted parameters and the challenge to the memory of the remote control Done by the embedded software in the remote control
- Display the decrypted parameters in a "Summary" page.
- Prompt the user to enter the PIN code.
- Build the acknowledgement ticket that will confirm the acceptance of these parameters by using the challenge, the parameters and the entered PIN code.
- Write the ticket in secured memory area of the remote control.
- Send said ticket to the MCU Done by the embedded software in the MCU
- Receive and write said ticket to the secured memory area of the MCU
- Encrypt said ticket by using a temporary key Ks2
- Send said encrypted ticket back to remote control Done by the embedded software in the remote control
- Send the encrypted ticket back to the medical device.

Done by the embedded software in the medical device
- Calculate the expected ticket
- Receive, decrypt and validate the acknowledgement ticket coming from the remote control.

This process is illustrated in the FIG. 4. When the ticket is validated the loopback process is closed and the medical device is allowed to use the updated parameters. This basic process can be more elaborated or part of a more complex scheme in order to improve the security of the secured pipe.

In one embodiment, said embedded software in the remote control is running by the host Operating System as defined above and said embedded software in the MCU is running by the medical Operating System as described above.

In one embodiment, the challenge may be encrypted too.

In one embodiment, the key Ks1 and Ks2 may be asymmetric key pair or symmetric key or use a hashing mechanism.

In one embodiment, the key Ks1 and Ks2 are same.

In one embodiment, the key Ks1 and Ks2 are different.

In one embodiment, the user has to enter a PIN code to confirm the entrance in loopback mechanism, such PIN code being entered on a random displayed array.

In another embodiment, the medical device comprises at least one sensor which may measure physiological properties of the patient, diagnostic means for recognizing in real time the first symptoms which are watched by said sensor and alarm means to alert the patient in case of said diagnostic means detect said first symptoms. In such way, the medical devices may monitor by the remote control and send alarm to a remote control.

In one embodiment, the remote control comprises a GPS for locating the user if the alarm is sent. Said medical assembly may launch an application in the remote control to locate the patient and to send said locating to a medical center or other person in case of said diagnostic means detect said first symptoms or/and if the patient can't do it himself. Also, said medical assembly may launch an application in the remote control to send data of physiological properties to a medical center or other person in case of said diagnostic means detect said first symptoms or/and if the patient can't do it himself.

The invention is of course not limited to the illustrated examples discussed previously.

The invention claimed is:

1. A medical system for securing a wireless communication, the medical system comprising:
   a medical device including a radio frequency communication device and internal memory storing information used to secure the wireless communication;
   a remote control device including a radio frequency communication device and a connection port, the radio frequency communication devices of the medical device and the remote control device configured to wirelessly communicate with each other; and
   a microcontroller configured to be connected to the connection port of the remote control device and having a secured memory storing key information having a secret key, the information of the medical device being exclusively paired with the secret key of the microcontroller, such that the medical device is exclusively paired with only one microcontroller out of a plurality of microcontrollers,
   wherein the information stored in the medical device includes information adapted to verify authenticity of the secret key of the microcontroller, such that only one microcontroller out of a plurality of microcontrollers can be authenticated, and the medical device is configured to accept communication with the remote control device only if (i) the microcontroller is connected to the remote control device, and (ii) the key information of the microcontroller was successfully authenticated,
   wherein the medical device and the microcontroller have been paired before the microcontroller is connected to the remote control device and before the microcontroller has been connected to any other remote control device,
   wherein the medical device that is exclusively paired with the microcontroller will not be discoverable by the remote control device unless the microcontroller is connected to the remote control device and has access to the key information.

2. The medical system according to claim 1, wherein the key information includes at least one of a configuration of the wireless communication and an encryption parameter of the wireless communication.

3. The medical system according to claim 1, wherein the remote control device includes a user interface having a display and input device.

4. The medical system according to claim 1, wherein the microcontroller includes a processor configured to generate additional key information for at least one of securing and initiating the wireless communication.

5. The medical system according to claim 1, wherein the microcontroller includes a processor configured to perform at least one of an encryption and a decryption of data of the wireless communication.

6. The medical system according to claim 1, wherein the microcontroller includes a processor for performing secured data processing.

7. The medical system according to claim 1, wherein the memory of the microcontroller further stores a link key used by the remote control device to initiate the wireless connection with the medical device.

8. The medical system according to claim 1, wherein the memory of the microcontroller further stores secured information which includes data unreadable by the remote control device.

9. The medical system according to claim 1, wherein the medical device cannot be paired another microcontroller.

10. The medical system according to claim 1, wherein the remote control device includes a second connecting port configured to receive a subscriber identity module (SIM) card of a telecom operator.

11. The medical system according to claim 1, wherein the remote control device includes a mobile virtualization display to show a controlled environment and uncontrolled environment.

12. The medical system according to claim 11, wherein the remote control device is operated by a host operating system and the controlled environment is a medical operating system.

13. The medical system according to claim 1, wherein the microcontroller and the medical device are each operated by computer instructions that are configured to perform a loopback mechanism when executed on the microcontroller and on the medical device.

14. The medical system according to claim 1, wherein the remote control device is a cell phone.

15. The medical system according to claim 1, wherein the microcontroller is a subscriber identity module (SIM) card of a telecom operator.

16. The medical system according to claim 1, wherein the microcontroller further stores at least one of the data and applications of a telephone operator.

17. A medical system for securing a wireless communication, the medical system comprising:
   a medical device including a radio frequency communication device, a processor, and internal memory storing information used to secure the wireless communication;
   a remote control device including a radio frequency communication device and a connection port, the radio frequency communication devices of the medical device and the remote control device configured to wirelessly communicate with each other; and
   a microcontroller configured to be connected to the connection port of the remote control device and having a memory storing key information , the information of the medical device being exclusively paired with the key information of the microcontroller, such that the medical device is exclusively paired with only one microcontroller out of a plurality of microcontrollers, wherein the medical device and the microcontroller have been paired before the microcontroller is connected to the remote control device and before the microcontroller has been connected to any other remote control device, wherein the memory of the medical device has computer instructions recorded thereon, the computer instruction configured to perform a method when executed on the processor of the medical device, the method including the steps of, generating a challenge;

encrypting data; and sending at least one of the generated challenge and the encrypted data to the remote control device, wherein the medical device that is exclusively paired with the microcontroller will not be discoverable by the remote control device unless the microcontroller is connected to the remote control device and has access to the key information.

18. The medical system according to claim 17, wherein the remote control device is a cell phone.

19. The medical system according to claim 17, wherein the microcontroller is a subscriber identity module (SIM) card of a telecom operator.

20. The medical system according to claim 17, wherein the microcontroller further stores at least one of the data and applications of a telephone operator.

21. A medical system for securing a wireless communication, the medical system comprising:

a medical device including a radio frequency communication device and internal memory storing information used to secure the wireless communication;

a remote control device including a radio frequency communication device and a connection port, the radio frequency communication devices of the medical device and the remote control device configured to wirelessly communicate with each other; and a microcontroller configured to be connected to the connection port of the remote control device, the microcontroller including a processor and a secured memory storing key information having a secret key, the information of the medical device being exclusively paired with the secret key of the microcontroller, such that the medical device is exclusively paired with only one microcontroller out of a plurality of microcontrollers, wherein the medical device and the microcontroller have been paired before the microcontroller is connected to the remote control device and before the microcontroller has been connected to any other remote control device, wherein the memory of the microcontroller has computer instructions recorded thereon, the computer instruction configured to perform a method when executed on the processor of the microcontroller, the method including the steps of, receiving, from the remote control device, at least one of an encrypted parameter and a challenge sent by the medical device;

decrypting encrypted data sent by the medical device with the secret key;

generating and encrypting data; and sending the encrypted data to the medical device via the remote control device, wherein the medical device that is exclusively paired with the microcontroller will not be discoverable by the remote control device unless the microcontroller is connected to the remote control device and has access to the key information.

* * * * *